US006783528B2

(12) United States Patent
Vincent-Prestigiacomo

(10) Patent No.: US 6,783,528 B2
(45) Date of Patent: Aug. 31, 2004

(54) POSITION-ADJUSTMENT SYSTEM FOR AN INSTRUMENT FOR SURGERY OF THE SPINE

(75) Inventor: Philippe Vincent-Prestigiacomo, Lacanau Océan (FR)

(73) Assignee: Stryker Spine (FR)

( * ) Notice: Subject to any disclaimer, the term of this patent is extended or adjusted under 35 U.S.C. 154(b) by 0 days.

(21) Appl. No.: 10/054,840

(22) Filed: Jan. 23, 2002

(65) Prior Publication Data

US 2002/0111627 A1 Aug. 15, 2002

(30) Foreign Application Priority Data

Jan. 23, 2001 (FR) .............................. 01 00873

(51) Int. Cl.[7] .................... A61B 17/56; A61B 17/58; A61F 2/30; A61F 5/00
(52) U.S. Cl. .......................... 606/61; 606/86
(58) Field of Search ................ 606/61, 86, 53, 606/103, 151; 24/136 R, 115 M

(56) References Cited

U.S. PATENT DOCUMENTS

| 731,635 | A | * | 6/1903 | Vandegrift | 403/46 |
| 1,258,580 | A | * | 3/1918 | Lassiter | |
| 3,758,922 | A | * | 9/1973 | Field | 24/115 R |
| 3,868,748 | A | * | 3/1975 | Kelly | 24/115 M |
| 4,653,481 | A | * | 3/1987 | Howland et al. | 606/61 |
| 4,881,302 | A | * | 11/1989 | Lee | 24/136 R |
| 5,074,864 | A | * | 12/1991 | Cozad et al. | 606/54 |
| 5,122,131 | A | * | 6/1992 | Tsou | 606/61 |
| 5,281,222 | A | * | 1/1994 | Allard et al. | 606/54 |
| 5,330,473 | A | * | 7/1994 | Howland | 606/61 |
| 5,507,746 | A | * | 4/1996 | Lin | 606/61 |
| 5,615,965 | A | * | 4/1997 | Saurat et al. | 403/24 |
| 5,653,708 | A | * | 8/1997 | Howland | 606/61 |
| 5,681,351 | A | * | 10/1997 | Jamiolkowski et al. | 606/232 |
| 5,682,796 | A | * | 11/1997 | Malone | 74/502.4 |
| 5,776,134 | A | * | 7/1998 | Howland | 606/61 |
| 5,888,197 | A | | 3/1999 | Mulac et al. | |
| 6,115,890 | A | * | 9/2000 | Silagy | 24/135 R |

FOREIGN PATENT DOCUMENTS

| DE | 199 60 718 A1 | 12/2000 |
| EP | 1 023 873 A2 | 8/2000 |
| WO | WO 98 29046 A1 | 7/1998 |

OTHER PUBLICATIONS

P.L. Pavy, Service De La Propriete Industrielle Brevet D'Invention Imprime et Edite le May 5, 1961. PRIX: 20 FR.

* cited by examiner

Primary Examiner—Eduardo C. Robert
Assistant Examiner—Anuradha Ramana
(74) Attorney, Agent, or Firm—Lerner, David, Littenberg, Krumholz & Mentlik, LLP

(57) ABSTRACT

A position-adjustment system having particular applicability for surgical instrumentation. The system comprises a body connected to an elongate member in such an arrangement as to have interchangeable locked and unlocked states. In the unlocked state, the body is free to move along the elongate member, and in the locked state the body is prevented from moving along the elongate member.

25 Claims, 3 Drawing Sheets

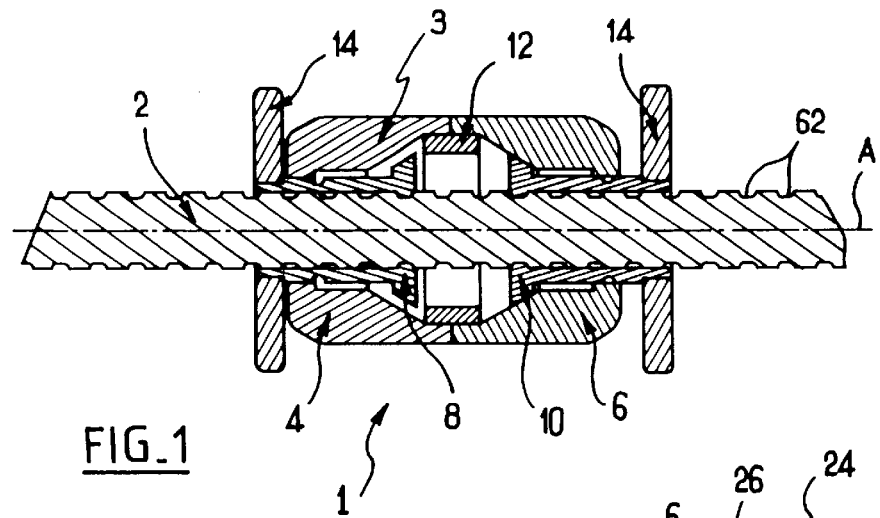
FIG_1
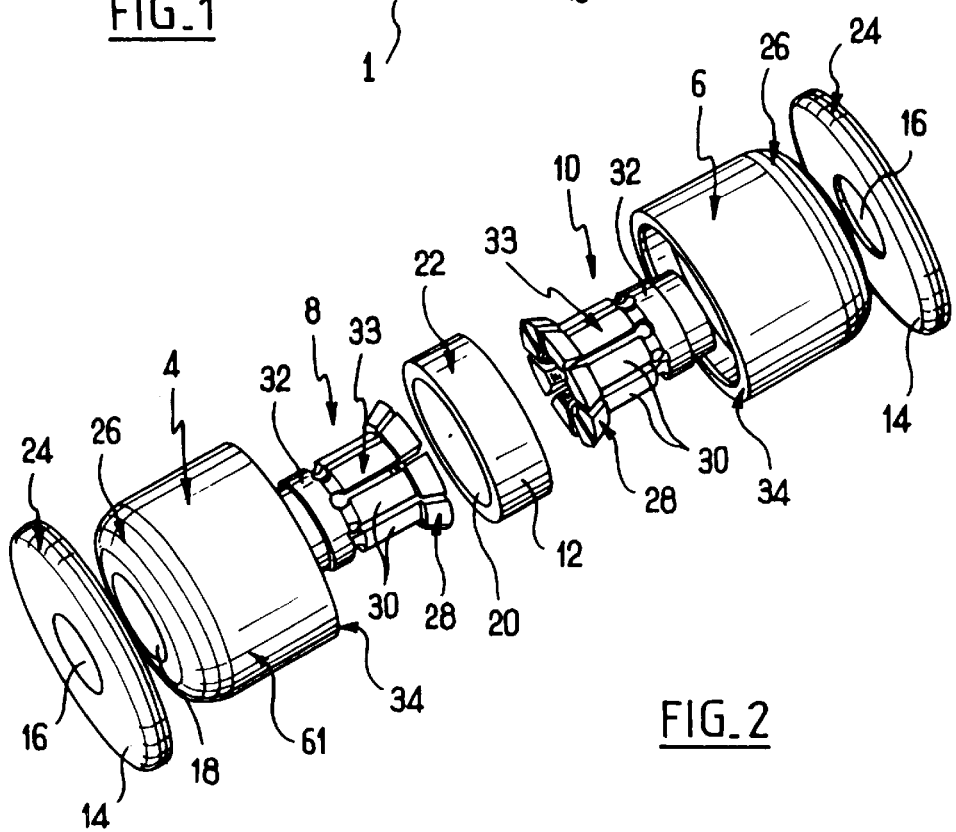
FIG_2

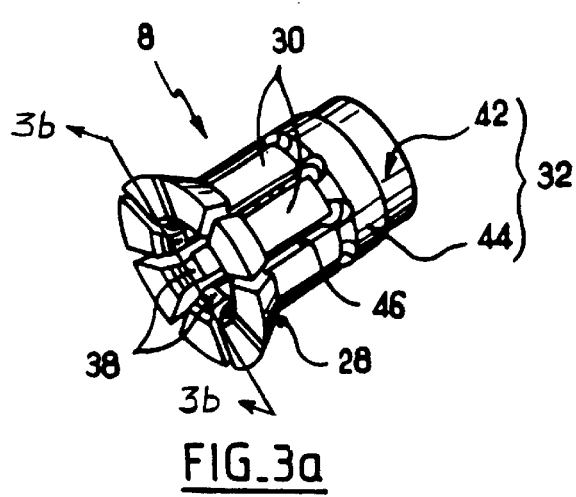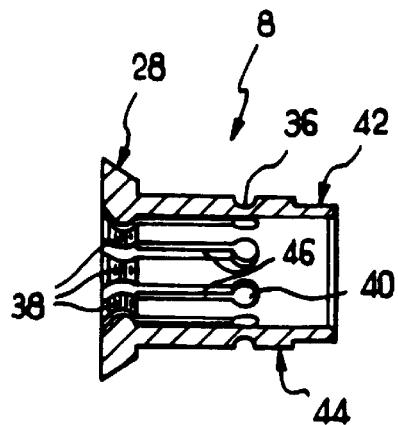
FIG.3a  FIG.3b
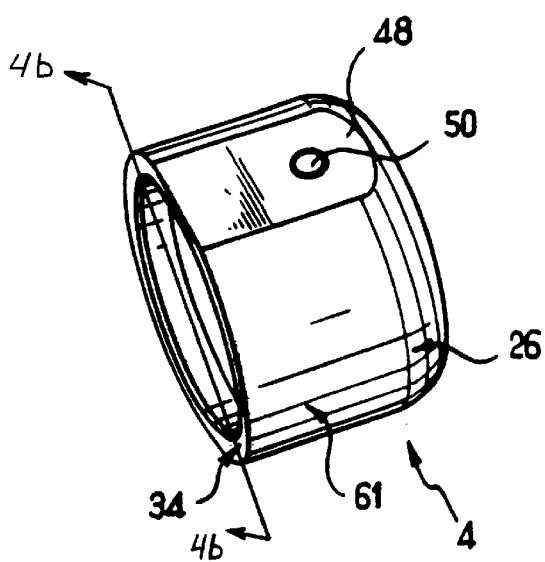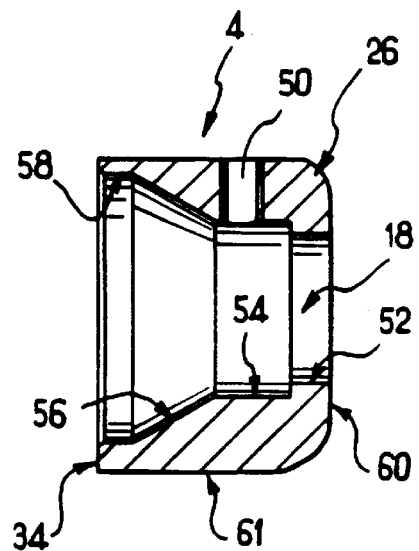
FIG.4a  FIG.4b

POSITION-ADJUSTMENT SYSTEM FOR AN INSTRUMENT FOR SURGERY OF THE SPINE

BACKGROUND OF THE INVENTION

The invention relates to a position adjustment system having particular applicability to surgical instrumentation.

In the event of traumas, simple or multiple fractures of one or more vertebrae in the spine can give rise to various configurations that require corrective movements to be applied in order to return the spine to its original shape, in particular concerning the curvature involved in lordosis and kyphosis. Special instruments are used for this purpose that make such restoration possible in co-operation with osteosynthesis systems that are known from elsewhere. Document DE G-91-12 466.2 describes such instrumentation including an adjustment system which comprises a threaded rod having two oppositely-handed threads situated on either side of drive means. Each of the threads engages in a tapped bore of a body connected to an element of the instrumentation. Operating such a system is lengthy because of the pitch of the threads and also because of the fact that during handling, surgical gloves come into contact with the threads which have sharp edges that are liable to catch and tear said gloves, thus requiring additional precautions to be taken. This lengthens the time required to perform an operation which increases the likelihood of harm to the patient.

SUMMARY OF THE INVENTION

An object of the invention is to provide an adjustment system for instrumentation for surgery of the spine, which can be put into place precisely and quickly.

To do this, according to the invention, there is provided a position-adjustment system, with particular applicability for. surgical instrumentation, in particular for surgery of the spine. The system comprises an elongate member, which, as known to those of ordinary skill in the art of surgical instrumentation, is suitable for being connected to a first element of the instrument. The system further comprises a body suitable for being fastened to the elongate member and for being connected to a second element of the instrument, as well as connection means for connecting the elongate member to the body. The system is arranged to have an unlocked state in which the connection means allow the elongate member to slide relative to the body and a locked state in which the connection means prevent the elongate member from sliding relative to the body.

Thus, the unlocked state enables adjustment of position to be performed simply, precisely, and quickly, while the locked state enables the selected position to be locked quickly. As a result, such a system can be operated simply, precisely, and quickly.

Advantageously, the connection means are arranged to prevent the elongate member from sliding relative to the body by a wedging effect.

Advantageously, the connection means comprise at least m one elastically deformable element.

Advantageously, the deformable element is suitable for implementing a wedging effect.

Advantageously, the system is arranged in such a manner that in the locked state, sliding is locked in a single direction.

Advantageously, the deformable element presents a bearing surface, and the elongate member presents a contact face suitable for coming into contact with the bearing surface in the locked state.

Thus, the longitudinal member entrains the deformable element towards the locked position because of the contact between the contact face and the bearing surface and without any intervention by the operator on the deformable element. The operator does not act on the deformable element, so the operator's hands do not come into contact with sharp edges. As a result there is no risk of damaging or tearing gloves during the operation.

Advantageously, the contact face is smooth, locking being obtained by friction.

Advantageously, the contact face is knurled.

Advantageously, the bearing surface includes knurling.

Advantageously, the contact face presents recesses, in particular grooves.

Advantageously, the bearing surface has a projection suitable for being received in the recesses.

Advantageously, the deformable element is split over all or part of its length.

Advantageously, the deformable element has deformable tongues at one end.

Advantageously, the deformable element has an end for implementing unlocking.

Advantageously, the deformable element is conical in shape.

Advantageously, the end for implementing unlocking includes a bearing rim.

Advantageously, the connection means include a second elastically deformable element.

Advantageously, the second deformable element is suitable for preventing sliding in the other direction of displacement.

Advantageously, the second deformable element is a mirror image of the first deformable element.

Advantageously, the body can be dismantled into at least two portions.

Advantageously, the body includes connection means for interconnecting the two portions, in particular, a ring.

BRIEF DESCRIPTION OF THE DRAWINGS

Other characteristics and advantages of the present invention appear from the following description of an embodiment. In the accompanying drawings:

FIG. 1 is a section view of an embodiment of the invention shown in full;

FIG. 2 is an exploded perspective view of the FIG. 1 embodiment without the elongate member;

FIG. 3a is a perspective view of the deformable element of the FIG. 1 embodiment of the invention;

FIG. 3b is a section view along line 3b through the deformable element of FIG. 3a;

FIG. 4a is a perspective view of a fraction of the body of the FIG. 1 embodiment of the invention;

FIG. 4b is a section view along line 4b of the FIG. 4a body portion;

DETAILED DESCRIPTION

Figure 5:
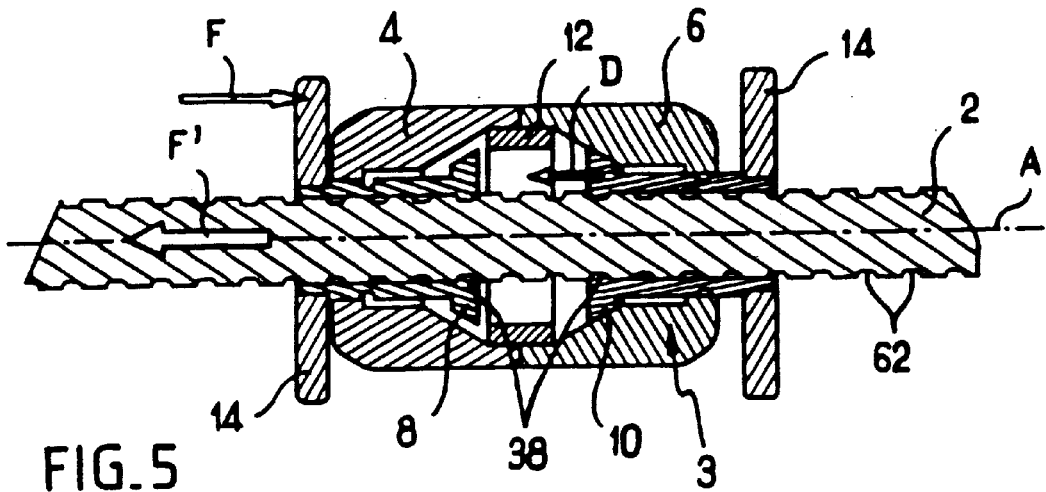
FIGS. 5 and 6 are section views through the FIG. 1 embodiment while it is in operation.

An embodiment of the invention is described with reference to the figures. In FIG. 1, the position-adjustment system 1 comprises a hollow body 3 suitable for slidably receiving an elongate member, or rod 2, of circular section, together with a pair of elastically deformable elements 8 and 10 each having a circular plate 14 fixed to one end thereof.

The hollow body 3 comprises two half-shells 4 and 6 interconnected by a ring 12. The half-shell 6 is a mirror image of the half-shell 4 about a plane perpendicular to the axis of revolution A of the body 3. Only one half-shell is therefore described in detail.

With reference to FIGS. 2, 4a, and 4b, the half-shell 4 has a through orifice 18 extending along its axis of revolution A. The half-shell 4 has an outside surface 61 and two axial end surfaces 34 and 60. The end surface 60 joins the outside surface 61 via a surface 26 of rounded shape. A portion of the outside surface 61 is replaced by a flat 48 parallel to the axis of revolution A. Perpendicular to this flat 48, a radial through tapped orifice 50 opens out to the inside of the orifice 18. The orifice 18 is made up of a plurality of portions: a cylindrical first portion of circular section defined by a surface 52 presents a first diameter; then a second cylindrical portion of circular section defined by a surface 54 presents a second diameter greater than the diameter of the first portion. The tapped orifice 50 opens out into this portion. A third portion, is in the form of a frustoconical surface 56 which extends the orifice 18 causing it to expand from the diameter of the second portion to the diameter of a fourth portion, itself defined by a forth cylindrical portion having a cylindrical surface 58 of circular section. It is explained below that the surface 56 forms a bearing surface.

The ring 12 for interconnecting the two symmetrical half-shells 4 and 6 has a cylindrical outside face 22 whose diameter is substantially equivalent to the diameter of the fourth portion of each of the half-shells. The ring 12 also presents a cylindrical inside surface 20. The length of the ring 12 is equivalent to twice the width of the fourth portion of each of the half-shells 4 and 6.

The body 3 is formed as follows: the ring 12 is inserted in the fourth portion of the orifice 18 of the first half-shell. Because of its double width, once the ring 12 has been put into place in the first half-shell, it projects from the face 34 of the half-shell. Thereafter, the second half-shell is engaged on the ring 12 until its face 34 comes to bear against the face 34 of the first half-shell. The body 3 is thus completely formed. The outside diameter of the ring 12 and the inside diameter of the fourth portion in each of the half-shells are selected in such a manner that the ring is inserted as a force-fit so as to be capable of holding the body 3 together while it is in use during surgery, while nevertheless remaining separable by a theatre nurse to enable the instrument to be cleaned completely between two operations. In order to make assembly more secure, a link element (not shown) can optionally be used to join the two half-shells 4 and 6 together. The link element may be fixed to the half-shells by means of threaded members (not shown) suitable for engaging the tapping in the orifices 50 of each of the half-shells 4 and 6, the link element being suitable for bearing against the flats 48.

With reference to FIGS. 2, 3a, and 3b, there follows a description of the deformable elements 8 and 10. The element 10 is a mirror image of the element 8 about a plane perpendicular to the axis of revolution A of said elements. Only one of the two elements is therefore described. The elastically deformable element 8 comprises two main portions 32 and 33. The general shape of the deformable element B is that of a tube. The portion 32 presents a first cylindrical surface 42 with a first diameter and a second surface 44 with a second diameter slightly greater than the diameter of the surface 42. The portion 32 is separated from the portion 33 of the deformable element 8 by a concave groove 36 forming a complete circle around the deformable element B and occupying a plane perpendicular to its axis. The portion 33 of the deformable element 8 is made up of a plurality of tongues 30 that are uniformly distributed over the entire circumference of the element 8. In this case, there are eight tongues 30. Each tongue 30 is separated from the next tongue by a slot 46 extending from the groove 36 to the free axial end of the portion 33 of the element 8. In the groove 36, each slot 46 becomes a circular through orifice 40. At the free end of the portion 33 of the deformable element 8, each tongue 30 is terminated by a projection extending radially outwards relative to the element 8 and presenting a surface 28 that is conical in shape. Still at its free end, opposite the surface 28 each tongue has a convex projection that is preferably of circular section extending radially towards the inside of the deformable element 8. As explained below, the portion 33 is the portion of the element 8 which deforms in use. This deformation is due to each tongue being suitable for deforming essentially in the vicinity of the groove 36.

The diameter of the surface 44 is substantially equivalent to the diameter of the first portion of the orifice 18 defined by the surface 52. The diameter of the surface 42 is substantially equivalent to the diameter of the orifice 16 present in the plates 14 that are described briefly below.

The plates 14 constitute rings each presenting a through orifice 16 and a rounded outer rim 24. The plates 14 are suitable for being mounted on the portion 32 of each of the deformable elements 8, 10, so as to cover its surface 42. With reference to FIG. 1, the elongate member 2 suitable for being received inside the body 3 is a circular section rod on the axis of revolution A and presenting a plurality of circumferential grooves 62 that are uniformly distributed along its entire length. These grooves 62 are of circular section.

The following is a description of how the position-adjustment system 1 is assembled. The first deformable element 8 is inserted in the half-shell 4, for example, in such a manner that the surface 44 occupies the first portion of the orifice 18, in contact with the surface 52. Thereafter, a first plate 14 is mounted as a force-fit on the portion 32 of the first deformable element 8 in such a manner that the orifice 16 of the plate 14 receives the surface 42 of the deformable element. Then the ring 12 is inserted as a force-fit into the fourth portion of the orifice 18 of the half-shell in such a manner that the surface 22 is in contact with the surface 58. Thereafter, the second deformable element 10 is inserted in the second half-shell 6 in the same manner as the deformable element 8 was inserted in the first half-shell 4, and then still in the same manner, the second plate 14 is put into place on the portion 32 of the deformable element 10. Finally, the second half-shell 6 is inserted on the ring 12 so as to close the body 3 as a whole. It should be observed that in each of the half-shells, each of the deformable elements is retained at one end by the presence of the plate 14 on its portion 32 and at its other end by the presence of the projections having surfaces 28 at the ends of the tongues 30 since each of the surfaces 28 is suitable for coming into contact with the surface 56 of the orifice 18. Secondly, when the plate 14 comes into contact with the rear face 60 of a half-shell, the surface 28 of each of the tongues 30 is spaced apart from the surface 56 of the half-shell. Conversely, when each of the surfaces 28 of each of the tongues 30 is in contact with the surface 56 of the half-shell, then the plate 14 is no longer in contact with the surface 60 of the half-shell. Finally, in use, the elongate member 2 is then inserted into the assembly.

Figure 6:
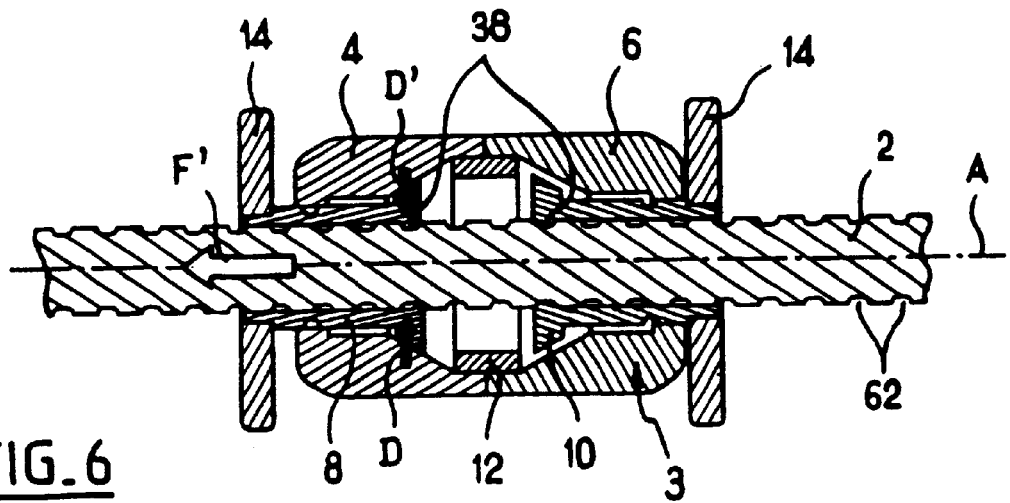
Figure 7:
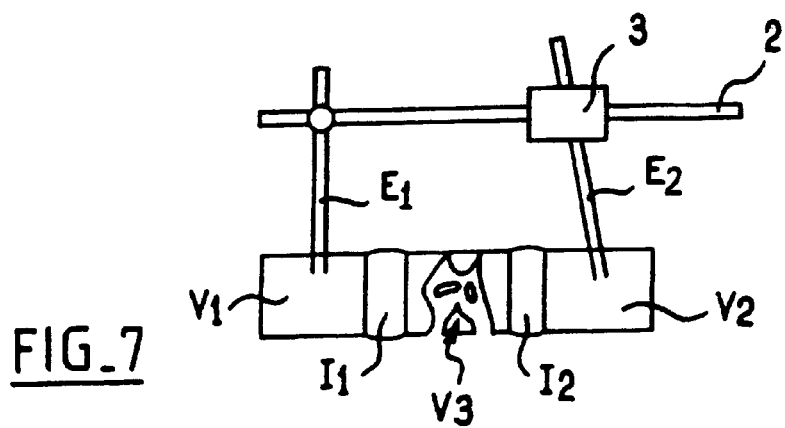
FIG. 7 is a diagrammatic view of the FIG. 1 embodiment in use in an operation.
Figure 5:
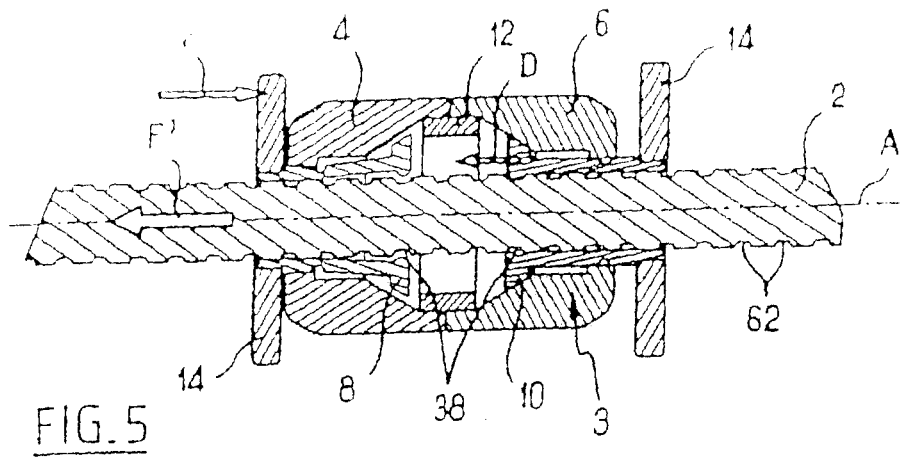
Figure 6:
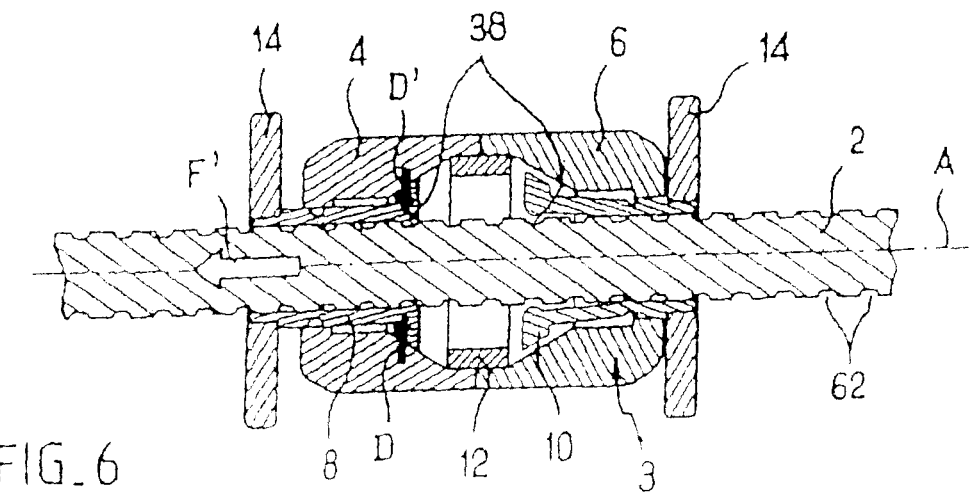

The operation of the position-adjustment system 1 is described below with reference to FIGS. 5, 6, and 7. A spinal column has a vertebra V3 which presents multiple fractures. This vertebra V3 is associated with two healthy vertebrae V1 and V2 on either side via vertebral disks I1 and I2. As it is known to those of ordinary skill in the art it is assumed that the elongate member 2 is connected to an element E1 of a surgical instrument that is engaged in the vertebra VI, while the body 3 is connected to a second element E2 of the same surgical instrument that is engaged with the vertebra V2.

The operation of moving the body 3 in the direction of arrow F is described with reference to FIG. 5. For this purpose, the operator applies a force F to the plate 14 connected to the deformable element 8. This force F enables the deformable element 8 to be moved so as to bring the plate 14 into contact with the face 60 of the half-shell 4 of the body 3, and separate the surfaces 28 of the blades 30 from contact with the surface 56 of the corresponding half-shell. As deformable element 8 moves in the direction of arrow F relative to body 3, by virtue of its circular projections 38 engaging a groove 62 in the elongate member 2, deformable element 8 entrains the elongate member 2 in the direction of arrow F. Thus elongate member 2 is also caused to move, relative to the body 3, in the direction of arrow F. Since the other deformable element 10 has its projections 38 engaged in another groove 62 of the elongate member 2, when the elongate member 2 is entrained in the direction of arrow F, this movement causes deformable element 10 to also move in the direction of arrow F until the surfaces 28 of each of the blades of the second deformable element 10 come into contact with the surface 56 of the half-shell 6. As a result, the second plate 14 connected to the second deformable element 10 is moved away from the face 60 of the second half-shell 6. FIG. 5 depicts this condition.

At this point, while maintaining force F on the first plate 14, the elongate member 2 may be moved in the direction of arrow F' , or as otherwise understood through relative movement, body 3 may be moved in the direction of arrow F relative to elongate member 2. Because the projections 38 and the grooves 62 are circular in shape, and because of the new position of deformable element 8 where there is now clearance to allow for the outward radial movement of the various tongues 30 which deform essentially at the groove 36, the projections 38 of the first deformable element 8 escape outwardly from the groove 62 of the elongate member 2 as the elongate member 2 moves in direction F' relative to the body 3, while force F is maintained on the first plate 14.

While moving in the direction of arrow F' relative to body 3, the elongate member 2 entrains the second deformable element 10 to move in direction D. This entrainment is similarly observed from the perspective of the body 3 moving in the direction of arrow F relative to elongate member 2. During this entrainment, the surfaces 28 of the second deformable element .10 move away from, and lose contact with, the surface 56 of the half-shell 6, thus moving into a position having a clearance space that will allow for the tongues 30 of the second deformable element 10 to move radially outwardly when necessary. The entrainment of the second deformable element 10 ends when the second plate 14 makes contact with the face 60 of the half-shell 6. At that point, with the continued application of force F on the first plate 14, body 3 may continue to be moved in the direction of arrow F relative to the elongate member 2 over an arbitrary distance, while the projections 38 of the second deformable element 10 move radially out of and into passing grooves 62 of the elongate member 2 which is moving in the direction F' relative to body 3.

Once the body 3 has reached the desired position, the operator ceases to apply the force F that was being exerted on the first plate 14. Deformable element 8 therefore gets entrained by the elongate member 2 moving in direction F' relative to the body 3, and, itself, moves in direction F' relative to body 3 until the faces 28 of each of the tongues 30 of the deformable element 8 come into contact with the surface 56 of the half-shell 4, thereby locking the assembly in position by holding the projections 38 in the groove 62 under a force D' generated by contact between the surface 56 and the surfaces 28. FIG. 6 depicts this condition.

Symmetrically, by acting on the second plate 14 in a manner identical to that described above, the operator can move the body 3 in the direction opposite to the arrow F Similarly, by acting on both plates 14 simultaneously as described above, the operator can cause the body 3 to slide in either direction an arbitrary distance along the elongate member 2 so as to position the body 3 at any desired location.

Naturally, numerous modifications can be made to the invention without thereby going beyond the ambit thereof.

For example, the grooves 62 of the elongate member 2 could be replaced by a knurled surface or by a smooth surface. Under such circumstances, the deformable elements could have a knurled surface instead of the projections 38. Locking in position would then be obtained by means of friction.

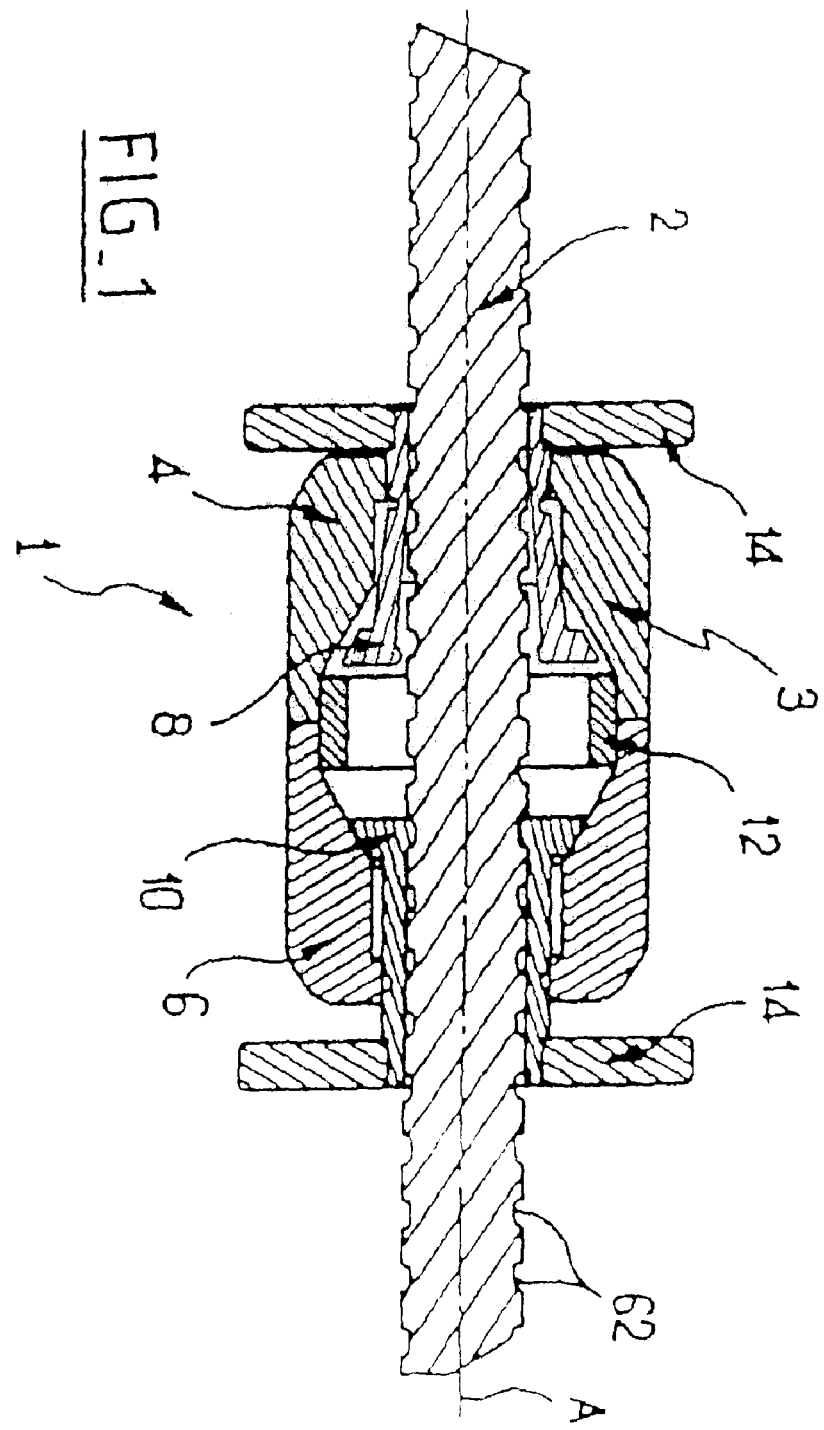

What is claimed is:

1. A position-adjustment system comprising:
an elongate member, and
a body suitable for being fastened to the elongate member,
the system comprising means for connecting the elongate member to the body and arranged to interchangeably have an unlocked state and a locked state, the unlocked state being one in which the means allow the elongate member to slide an unlimited displacement in a first direction relative to the body and a locked state being one in which the means prevent the elongate member from sliding relative to the body.

2. The position-adjustment system according to claim 1, wherein the means for connecting the elongate member to the body includes at least one release element to facilitate placing the means for connecting the elongate member to the body into the locked and unlocked states.

3. The position-adjustment system according to claim 2, further including a second release element.

4. The position-adjustment system according to claim 1, wherein the body can be dismantled into at least two portions.

5. The position-adjustment system according to claim 4, wherein the body includes means for interconnecting the two portions.

6. The position-adjustment system according to claim 5, wherein the means for interconnecting the two portions is a ring.

7. The position-adjustment system according to claim 1, wherein the means for connecting the elongate member to the body are arranged to prevent the elongate member from sliding relative to the body by a wedging effect.

8. The position-adjustment system according to claim 7, wherein the means for connecting the elongate member to the body comprise at least one elastically deformable element, and wherein the deformable element is suitable for implementing a wedging effect.

9. The position-adjustment system according to claim 7, wherein the system is arranged in such a manner that in the locked state, sliding is prevented in a single direction of displacement.

10. The position-adjustment system according to claim 1, wherein the means for connecting the elongate member to the body comprise at least one elastically deformable element.

11. The position-adjustment system according to claim 10, wherein the elastically deformable element presents a bearing surface, and the elongate member presents a contact face suitable for coming into contact with the bearing surface in the locked state.

12. The position-adjustment system according to claim 11, wherein the contact face is smooth, locking being obtained by friction.

13. The position-adjustment system according to claim 11, wherein the contact face is knurled.

14. The position-adjustment system according to claim 11, wherein the bearing surface includes knurling.

15. The position-adjustment system according to claim 11, wherein the contact face presents recesses.

16. The position-adjustment system according to claim 15, wherein the bearing surface has a projection suitable for being received in the recesses.

17. The position-adjustment system according to claim 15, wherein the recesses are grooves.

18. The position-adjustment system according to claim 10, wherein the deformable element is split over all or part of its length.

19. The position-adjustment system according to claim 10, wherein the deformable element has deformable tongues.

20. The position-adjustment system according to claim 10, wherein the deformable element has an end for implementing unlocking.

21. The position-adjustment system according to claim 20, wherein the end for implementing unlocking includes a bearing rim.

22. The position-adjustment system according to claim 10, wherein the deformable element is generally conical in shape.

23. The position-adjustment system according to claim 10, wherein the means for connecting the elongate member to the body include a second elastically deformable element.

24. The position-adjustment system according to claim 23, wherein the second deformable element is suitable for preventing sliding opposite the first direction of displacement.

25. The position-adjustment system according to claim 23, wherein the second deformable element is a mirror image of the first deformable element.

* * * * *

UNITED STATES PATENT AND TRADEMARK OFFICE
CERTIFICATE OF CORRECTION

PATENT NO. : 6,783,528 B2
DATED : August 31, 2004
INVENTOR(S) : Philippe Vincent Prestigiacomo It is certified that error appears in the above-identified patent and that said Letters Patent is hereby corrected as shown below:

Title page, Item [54] and Column 1, line 1,
Title, should read -- POSITION-ADJUSTMENT SYSTEM WITH APPLICABILITY FOR SURGICAL INSTRUMENTATION --.

Column 1,
Line 35, after "for" delete ".".
Line 58, before "one" delete "m".

Column 5,
Line 57, after "element" delete ".".

Column 8,
Line 5, "10" should read -- 18 --.

Signed and Sealed this

Twenty-second Day of March, 2005

JON W. DUDAS
*Director of the United States Patent and Trademark Office*

UNITED STATES PATENT AND TRADEMARK OFFICE
CERTIFICATE OF CORRECTION

PATENT NO. : 6,783,528 B2
DATED : August 31, 2004
INVENTOR(S) : Philippe Vincent Prestigiacomo It is certified that error appears in the above-identified patent and that said Letters Patent is hereby corrected as shown below:

Drawings,
Sheet 1 of 3, replace FIG 1 with FIG. 1 in Replacement Sheet.
Sheet 3 of 3, replace FIGS. 5 and 6 with FIGS. 5 and 6 in Replacement Sheet.

Signed and Sealed this

Sixth Day of June, 2006

JON W. DUDAS
*Director of the United States Patent and Trademark Office*